(12) United States Patent
Ramstad et al.

(10) Patent No.: US 6,833,238 B2
(45) Date of Patent: Dec. 21, 2004

(54) PETAL-ARRAY SUPPORT FOR USE WITH MICROPLATES

(75) Inventors: Paul O. Ramstad, San Jose, CA (US); Michael P. Harrold, San Mateo, CA (US); Kevin M. Hennessy, San Mateo, CA (US); Aldrich N. K. Lau, Palo Alto, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/413,935

(22) Filed: Apr. 14, 2003

(65) Prior Publication Data

US 2003/0228706 A1 Dec. 11, 2003

Related U.S. Application Data

(63) Continuation-in-part of application No. 10/038,974, filed on Jan. 4, 2002, now Pat. No. 6,632,660.
(60) Provisional application No. 60/398,852, filed on Jul. 26, 2002.

(51) Int. Cl.[7] .................................................. C12Q 1/00
(52) U.S. Cl. ..................... 435/4; 435/288.4; 435/288.6; 435/297.5; 435/305.2; 210/660
(58) Field of Search ............................ 435/4, 325, 410, 435/243, 287.3, 288.4, 305.2, 309.1, 395, 288.6, 297.1, 297.5; 210/660

(56) References Cited

U.S. PATENT DOCUMENTS

| | | |
|---|---|---|
| 2,636,851 A | 4/1953 | Juda et al. |
| 3,247,133 A | 4/1966 | Chen |
| 3,304,272 A | 2/1967 | Zenftman |
| 3,723,306 A | 3/1973 | Bridgeford |
| 3,915,639 A | 10/1975 | Friedenberg |
| 3,965,039 A | 6/1976 | Chaplits et al. |
| 4,100,149 A | 7/1978 | Meiller et al. |
| 4,187,333 A | 2/1980 | Rembaum et al. |
| 4,414,111 A | 11/1983 | Iwaisako et al. |
| 4,515,906 A | 5/1985 | Friesen et al. |

(List continued on next page.)

FOREIGN PATENT DOCUMENTS

| | | |
|---|---|---|
| EP | 0407560 B1 | 6/1995 |
| GB | 693166 | 6/1953 |
| JP | 2830107 B2 | 3/1991 |
| JP | 2001009274 A | 1/2001 |
| KR | 8001597 | 12/1980 |
| WO | WO 99/21958 A1 | 5/1999 |
| WO | WO 99/22868 A1 | 5/1999 |
| WO | WO 00/66995 A2 | 11/2000 |
| WO | WO 01/21310 A2 | 3/2001 |
| WO | WO 02/50260 A2 | 6/2002 |

OTHER PUBLICATIONS

Alpert et al., *J. Chromatog.* 185, 375 (1979).
Haller, Wolfgang, "Solid Phase Biochemistry," Chapter 11, *John Willy & Sons*, New York, (1983).
Tai, et al., *Polym. National Sci Eng.*, 86, 235 (2002).

(List continued on next page.)

*Primary Examiner*—David A. Redding (57) ABSTRACT

Devices are provided which include supports upon which one or more ion-exchange materials can be disposed for purifying a sample. In various embodiments, the supports include a plurality of deformable members, for example, petal-shaped purification members, that provide binding sites for ion-exchange material and optionally biochemical species, chemicals, salts, or other materials. An apparatus and method are also provided for the insertion and removal of the purification members into respective wells of a multi-well microplate.

23 Claims, 8 Drawing Sheets

U.S. PATENT DOCUMENTS

| | | |
|---|---|---|
| 4,537,911 A | 8/1985 | Chonde |
| 4,564,644 A | 1/1986 | Harris |
| 4,612,247 A | 9/1986 | Walsh et al. |
| 4,675,384 A | 6/1987 | Dromard et al. |
| 4,717,425 A | 1/1988 | Lefebvre |
| 4,935,342 A | 6/1990 | Seligson et al. |
| 4,948,814 A | 8/1990 | Motozato et al. |
| 4,997,932 A | 3/1991 | Reardon et al. |
| 5,057,426 A | 10/1991 | Henco et al. |
| 5,064,866 A | 11/1991 | Toyomoto et al. |
| 5,081,160 A | 1/1992 | Strom et al. |
| 5,213,766 A | 5/1993 | Flesher et al. |
| 5,244,929 A | 9/1993 | Gottlieb et al. |
| 5,250,188 A | 10/1993 | Bruening et al. |
| 5,258,503 A | 11/1993 | Yokohari et al. |
| 5,264,100 A | 11/1993 | Shimohira et al. |
| 5,278,193 A | 1/1994 | Eiffler et al. |
| 5,279,744 A | 1/1994 | Itoh et al. |
| 5,288,763 A | 2/1994 | Li et al. |
| 5,316,680 A | 5/1994 | Frechet et al. |
| 5,356,937 A | 10/1994 | Eiffler et al. |
| 5,437,979 A | 8/1995 | Rampal et al. |
| 5,438,128 A | 8/1995 | Nieuwkerk et al. |
| 5,536,644 A | 7/1996 | Ullman et al. |
| 5,633,290 A | 5/1997 | Frechet et al. |
| 5,654,141 A | 8/1997 | Mariani et al. |
| 5,707,812 A | 1/1998 | Horn et al. |
| 5,747,663 A | 5/1998 | Colpan et al. |
| 5,834,633 A | 11/1998 | Davison |
| 5,837,520 A | 11/1998 | Shabram et al. |
| 5,856,192 A | 1/1999 | Bloch |
| 5,936,004 A | 8/1999 | Altmeier |
| 5,962,250 A | 10/1999 | Gavin et al. |
| 5,990,301 A | 11/1999 | Colpan et al. |
| 6,008,036 A | 12/1999 | Fanget et al. |
| 6,124,092 A | 9/2000 | O'Neill et al. |
| 6,136,555 A | 10/2000 | Jones |
| 6,241,980 B1 | 6/2001 | Collis et al. |
| 6,270,970 B1 | 8/2001 | Smith et al. |
| 6,340,589 B1 | 1/2002 | Turner et al. |
| 6,380,456 B1 | 4/2002 | Goldman |
| 6,416,716 B1 | 7/2002 | Shukla et al. |
| 6,504,021 B2 | 1/2003 | Kristyanne et al. |
| 6,521,342 B1 | 2/2003 | Hutter et al. |
| 6,521,343 B1 | 2/2003 | Samaranayake et al. |
| 6,531,523 B1 | 3/2003 | Davankov et al. |
| 6,632,660 B2 * | 10/2003 | Ramstad .................. 435/305.2 |
| 2002/0052006 A1 | 5/2002 | Dunayevskiy et al. |
| 2002/0168643 A1 | 11/2002 | Wierzbowski et al. |
| 2003/0012697 A1 | 1/2003 | Hahn et al. |
| 2003/0098271 A1 | 5/2003 | Somack et al. |

OTHER PUBLICATIONS

Tan, Hongdong et al., "Automation and Integration of Multiplexed On–Line Sample Preparation with Capillary Electrophoresis for High–Throughput DNA Sequencing,"*Analytical Chemistry*, 1998, vol. 70, 4044–4053.

PCT International Search Report for International application no. PCT/US03/23253 dated Jan. 22, 2004.

* cited by examiner

PETAL-ARRAY SUPPORT FOR USE WITH MICROPLATES

RELATED APPLICATIONS

This application is a continuation-in-part of U.S. patent application Ser. No. 10/038,974 to Paul O. Ramstad, filed Jan. 4, 2002 now U.S. Pat. No. 6,632,660, incorporated herein in its entirety by reference. This application claims priority from U.S. patent application Ser. No. 10/413,797, filed Apr. 14, 2003 to Hennessy et al., entitled "Device and Method for Purification of Nucleic Acids," U.S. patent application Ser. No. 10/414,179, filed Apr. 14, 2003, to Lau et al., entitled "Size-Exclusion Ion-Exchange Particles)" and U.S. Provisional Patent Application No. 60/398,852 filed Jul. 26, 2002. All above-cited applications are incorporated herein in their entireties by reference.

BACKGROUND

There has been a desire in recent years to develop methods for purifying biochemical solutions and mixtures that contain target molecules or compounds and impurities. Various methods have been used purifying biological samples and include contacting a sample with an ion-exchange resin. There continues to be a need for fast and efficient methods and devices for purifying a biological sample.

SUMMARY

According to various embodiments, an apparatus is provided having a petal-array of purification materials that can be disposed within respective wells of a multi-well microplate, for example, a standard-format 96- or 384-well plate. Methods of making and using the apparatus are also provided. The purification material can be located on an array of members, for example, petal-shaped purification members, adapted for insertion into a corresponding array of reaction wells. The purification members can also include binding sites for target components. An apparatus and method for facilitating the release of labeled monomers from a purification and binding support within a microplate format, are also provided.

According to various embodiments, an analyte-manipulation apparatus is provided. The apparatus can include, for example, a plurality of wells defining an array, wherein each of the wells includes a rim defining an opening at an upper end of each well, with the openings being disposed within a first plane. The apparatus can include a support, for example, a sheet, including a plurality of petal-shaped purification or ion-exchange members formed therein at positions corresponding to the wells of the array, with the support being disposed along a second plane above and substantially parallel to the first plane, and with at least one of the petal-shaped purification members being positioned near each one of the openings. According to various embodiments, the apparatus can include a stack of supports, for example, formed as individual sheets, disposed above the well openings, with each support of the stack including a plurality of petal-shaped purification members integrally formed therein, and with each petal-shaped purification member of each support being disposed at a position corresponding to a respective one of the wells of the array. The stack of supports can include more than one support, for example, at least three of the supports, for example, 3, 4, 5, 6, 7, 8, 9, 10, or more supports. Each of the petal-shaped purification members can be movable between (i) a first position, substantially within the second plane, and (ii) a second position, at least partially disposed outside of the second plane and extending at least partially into a nearby well via a respective opening. The apparatus can further include a platen including a major surface facing the support, and a plurality of ring-shaped projections extending outwardly from the major surface of the platen. The platen can be adapted for movement toward and away from the support, whereby upon moving the platen toward the support, the projections can pressingly engage the petal-shaped purification members, thereby deflecting the petal-shaped purification members from the first position to the second position. Each of the ring-shaped projections can taper in a direction away from the major surface.

According to various embodiments, the platen and each of the ring-shaped projections of the platen defines a passage extending longitudinally through each ring-shaped projection and through the platen. An instrument, for example, a pipette, can be inserted through the passage to access the interior region of any one or more of the wells when the petal-shaped purification members are deflected into their respective wells. For example, a sample and/or reagent can be deposited into or withdrawn from one or more selected wells by using an instrument via the passage.

According to various embodiments, the apparatus can further include a die plate disposed between the support and the plurality of wells, wherein the die plate includes an array of apertures extending therethrough, with each of the apertures being disposed at a position corresponding to a respective one of the wells of the array.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description below.

BRIEF DESCRIPTION OF THE DRAWINGS

The present teachings can further be understood by reference to the following description taken in conjunction with the accompanying drawings, in which identical reference numerals identify identical or similar elements, and in which.

DETAILED DESCRIPTION OF CERTAIN EMBODIMENTS

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present teachings. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "a monomer" includes two or more monomers, According to various embodiments, size-exclusion ion-exchange (SEIE) particles having an ion-exchange core micro-encapsulated by a shell capable of size-exclusion are provided. The terms "micro-encapsulation," "micro-encapsulated," or the like, refer to a process of encapsulation on the individual particle level. In one embodiment, a core of liquid, solid, and/or gas is micro-encapsulated with a shell to control access to the core. In various other embodiments, micro-encapsulation can coat the entire exterior surface of the core (and optionally interior surfaces), or it can coat only a portion of the exterior surface of the core (and optionally interior surfaces). In various other embodiments, micro-encapsulation of the core can be irreversible to permanently coat the core, or reversible to release the core upon dissolution of the coating. According to various embodiments, micro-encapsulation can include encapsulation of an agglomerate of core material in a shell. The aggregate can be fused, sintered, pressed, compressed, or otherwise formed together core materials. According to various embodiments, the core material can be a single particle and not an aggregate. As used herein, the term "core" or "core material" can refer to a single particle or an aggregate of particles. The term "shell" refers to coating any portion of the core exterior surface and/or interior surface. The dimensions and formation of the shell are described below. The term "material" refers to any substance on a molecular level or in bulk. As used below, a material can be a liquid and/or solid, e.g. an emulsion or a resin.

As used herein, a "mixture" can refer to more than one SEIE particle used together in a packed column, a mixed-bed, a homogenous bed, a fluidized bed, a static column with continuous flow, or a batch mixture, for example. The mixture can include size-exclusion cation-exchange particles and size-exclusion anion-exchange particles, size-exclusion cation-exchange particles and anion-exchange particles, size-exclusion anion-exchange particles and cation-exchange particles, SEIE particles and inerts, or a combination thereof. The mixture can include any physical configuration known in the art of separations, and any chemical mixture known in the art of ion exchange.

Reference will now be made to various embodiments of the present teachings, examples of which are illustrated in the accompanying drawings. While the present teachings will be described in conjunction with various embodiments, it will be understood that they are not intended to limit the present teachings. On the contrary, the present teachings are intended to cover alternatives, modifications, and equivalents, which may be included within the present teachings.

According to various embodiments, methods of providing an array of solid supports or binding sites within wells of a microplate, for example, a standard-format 96- or 384-well plate, are provided. Also provided are methods for facilitating the release of species, for example, labeled monomers, from one or more support, wherein the one or more support can be in a microplate format.

Figure 1:
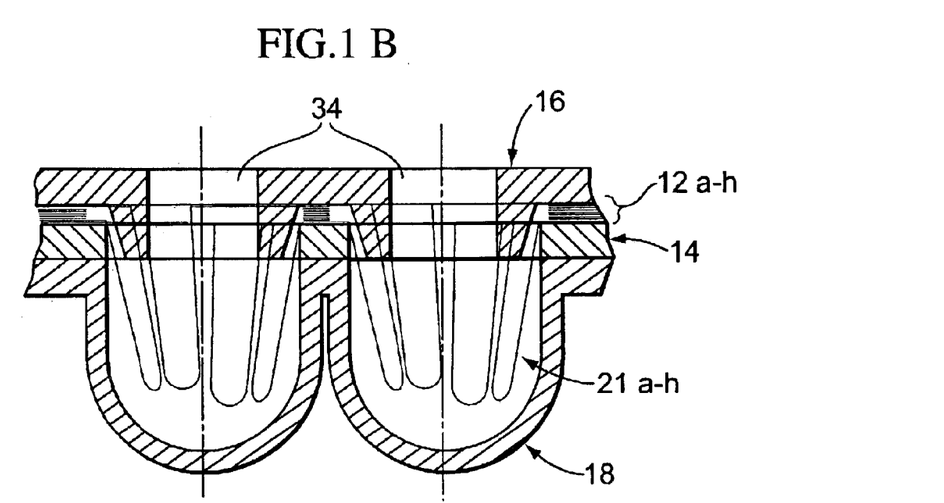
FIGS. 1A and 1B are partial side-sectional views of an apparatus according to various embodiments.
Figure 1A:
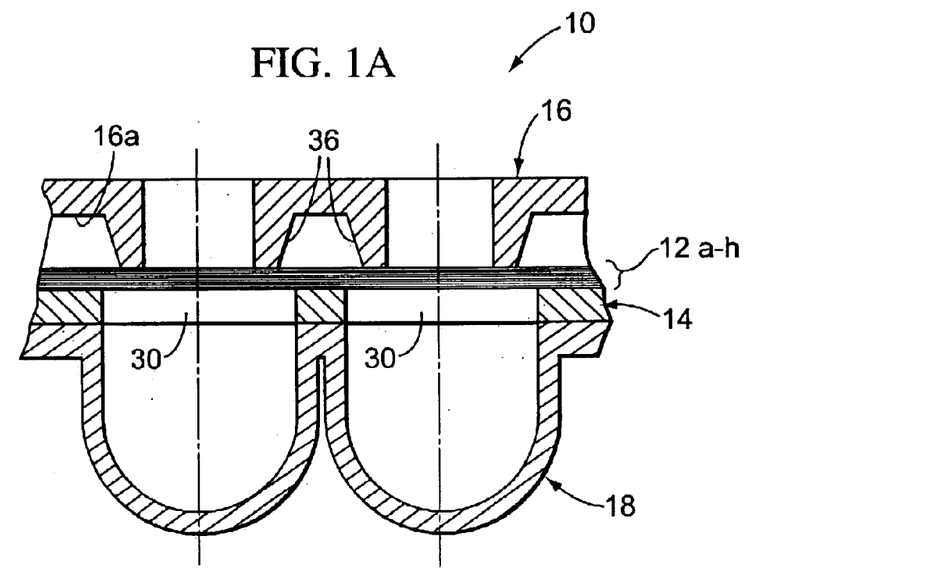
Figure 2:
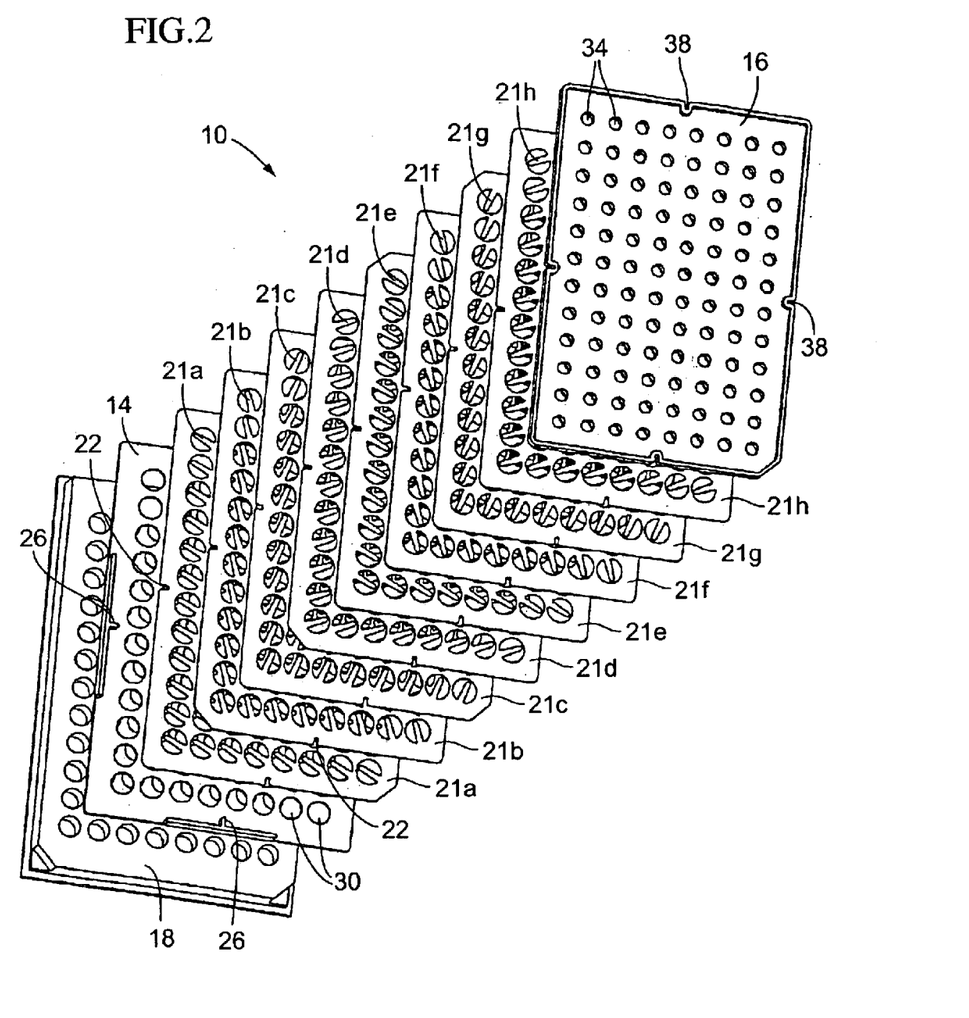
FIG. 2 is an exploded, perspective view of the apparatus shown in FIG. 1A.

According to various embodiments, and with initial reference to FIGS. 1A and 2, an apparatus 10 can include one or more supports, for example, the stack of support sheets 12a–h. The number of supports can be any suitable number, for example, 2, 3, 4, 5, 6, 7, 8, 9, 10, or more. As shown in FIGS. 1A and 2, the support sheets 12a–h can be situated between a die plate 14 and a platen 16, wherein the die plate 14 is located above microplate 18.

The support sheets 12a–h can be formed of any suitable material, for example, a membrane or film material. According to various embodiments, each of the support sheets 12a–h independently can include a polymeric film, for example, a polycarbonate or polystyrene film, having a thickness of between about 0.001 inch and about 0.010 inch, for example, about 0.004 inch. The film can be textured to increase its effective surface area. According to various embodiments, each support sheet can be a die-cut, chemically-treated, membrane or film support.

Figure 3:
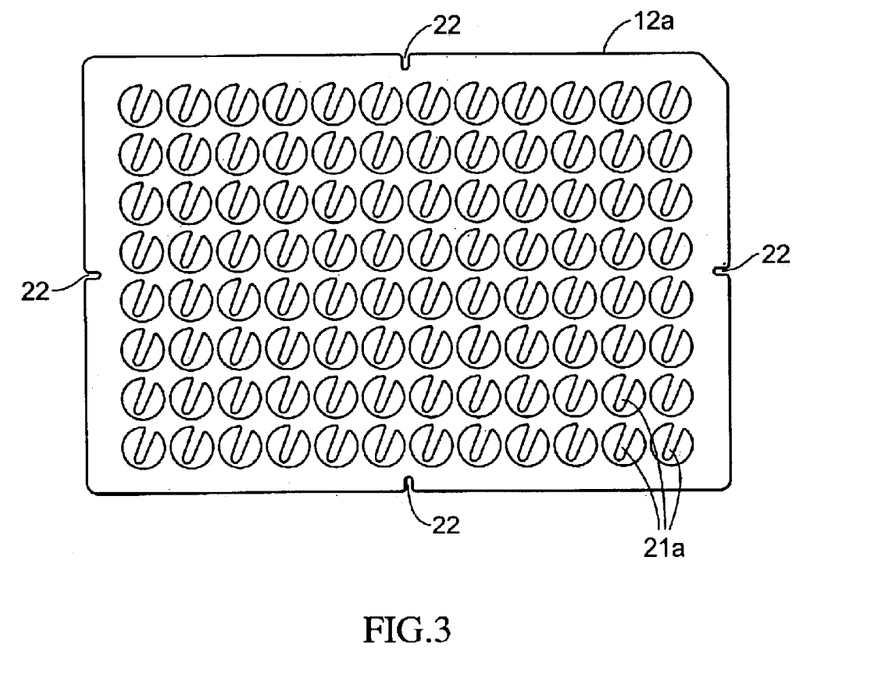
FIG. 3 is a top plan view showing a support including petal-shaped purification members according to various embodiments.

FIG. 3 shows a single support sheet, 12a, from the stack of support sheets 12a–h of FIG. 2, in top plan view. Support sheet 12a can be configured with outer dimensions generally like that of a top surface of a microplate with which the support sheet 12a is to be used. Support sheet 12a can be die-cut to provide an array of members, for example, petal-shaped purification members 21a. The members can be any suitable shape, for example, petal-shaped, rectangular, or finger-shaped. The petal-shaped purification members 21a can be arranged in an array corresponding to an array of wells in the microplate 18 with which the support is to be used, for example, a regular rectangular array. In the illustrated arrangement, the petal-shaped purification members are arranged in a 12×8 array, with adjacently disposed petal-shaped purification members being spaced 0.9 cm center-to-center. Other array configurations are contemplated herein, for example, a 24×16 array, with adjacently disposed petal-shaped purification members being spaced 0.45 cm center-to-center. Other suitable configurations will be apparent to those of ordinary skill in the art upon review of the disclosure and/or practice of the present teachings as described herein.

Each of the support sheets 12a–h can include one or more location features to facilitate alignment with respect to other system components. For example, as shown in FIGS. 2 and 3, slots 22 can be formed at selected locations along the edge regions of each of the support sheets 12a–h. The slots 22 can be positioned and configured to mate with complementary-shaped regions of one or more of the microplate 18, die plate 14, and platen 16. For example, FIG. 2 shows a protrusion 26 capable of mating with the slots 22, wherein the protrusion 26 is formed at a mid-point along each edge region of the die plate 14.

Figure 4:
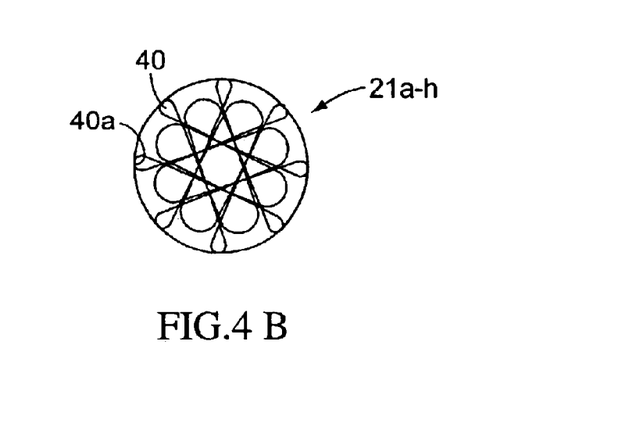
FIGS. 4A and 4B are enlarged top plan views showing a plurality of petal-shaped purification members, each taken from a respective support of an aligned stack of eight supports, individually and superposed, respectively.
Figure 4A:
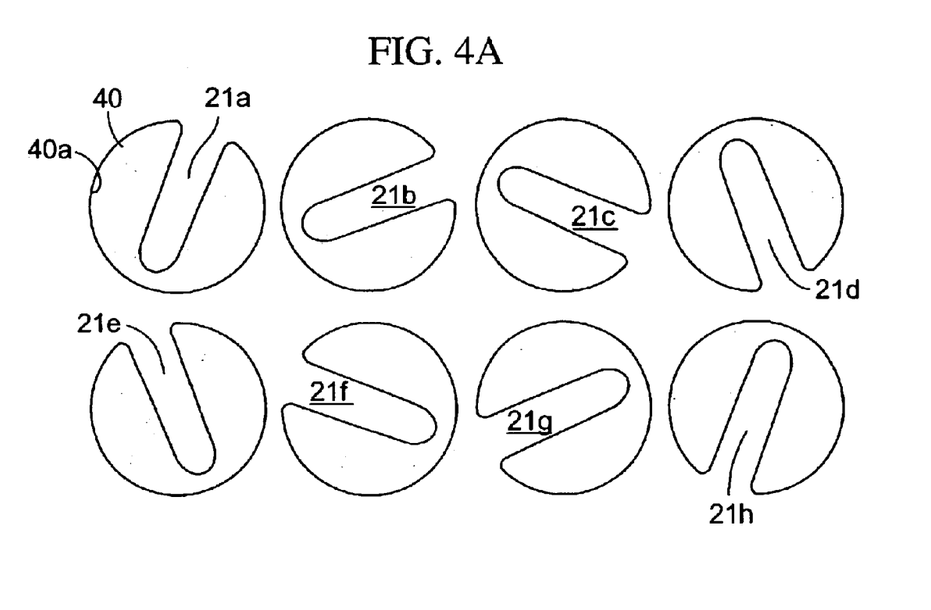

According to various embodiments, all the petal-shaped purification members of any one of the supports can face, or "point," in the same direction. The directionality of the petal-shaped purification members can differ between any two of the supports. That is, the petal-shaped purification members of any one support can point in a direction that differs from that of any of the other supports. In the embodiment of FIG. 2, for example, it can be seen that each support includes a petal-shaped purification member disposed at a position that is radially distinct from the petal-shaped purification members of the other supports of the stack. FIG. 4A shows petal-shaped purification members 21a–h from a selected coordinate, for example, row 1, column 1, of each of the eight supports 12a–h of the stack from FIG. 2. The petal-shaped purification members are shown with each in the orientation it would be in when the eight supports are stacked and aligned for use, for example, as shown in FIGS. 1A and 2. Each of the die-cut portions of the support can define a circular open region 40 having a circumferential edge 40a, with its respective petal-shaped purification member 21a–h extending into the circular open region from a unique position along the circumferential edge. FIG. 4B shows the petal-shaped purification members from FIG. 4A superposed one over the other as they would be when disposed in an aligned stack. The eight petal-shaped purification members 21a–h in FIG. 4B can be seen extending inwardly into a common circular open region 40 from regularly spaced positions about the circumferential edge 40a of the circular open region 40.

According to various embodiments, each of the petal-shaped purification members 21a–h can be deformable from a normal position, substantially within a plane defined by the sheet, to a second position, at least partially disposed outside of such plane. The petal-shaped purification members can be resilient such that they return to their normal position after a deforming force in discontinued. Due to the deformable quality of the petal-shaped purification members, applying a downwardly-directed force against a petal-shaped purification member can deflect the member from its normal position to a second position, for example, below the plane of the support. Upon removing the force, the resilient petal-shaped purification member can return substantially to its normal position.

Figure 5:
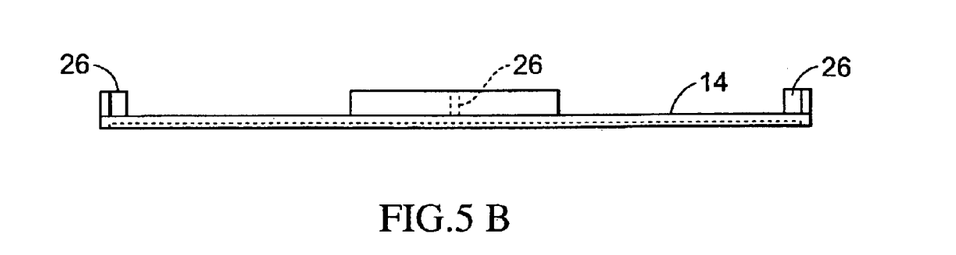
FIGS. 5A and 5B show a die plate, according to various embodiments, in top plan view and side elevational view, respectively.
Figure 5A:
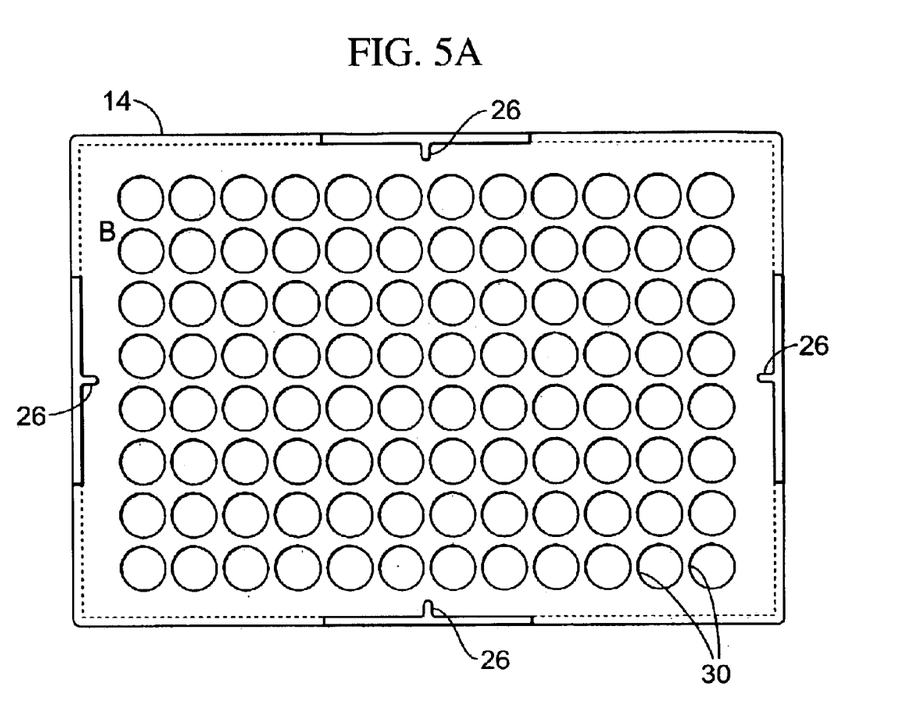

FIGS. 5A and 5B show the die plate 14 in top plan and side elevational views, respectively. The die plate 14 can include protrusions 26 for properly locating and aligning one or more supports thereon, for example, by way of slots 22 in supports 12a–h. Use of location features can facilitate location of an array of petal-shaped purification members of a support directly over respective well openings in a microplate. The die plate 14 can include an array of holes or apertures 30 that are concentric, and directly correspond to, the wells of the microplate 18. The die plate can include features that align it relative to the microplate 18, and/or to the platen 16.

Figure 6:
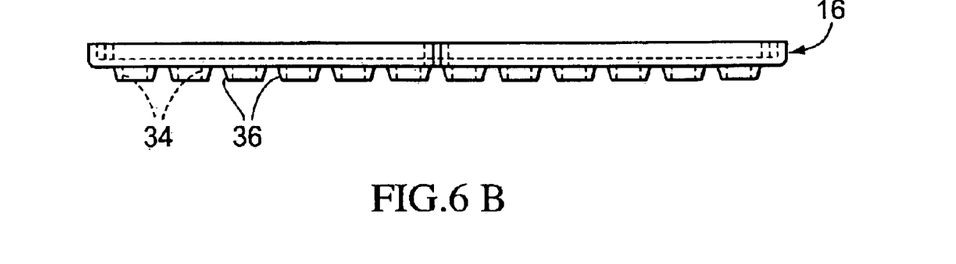
FIGS. 6A and 6B show a platen, according to various embodiments, in top plan view and side elevational view, respectively.
Figure 6A:
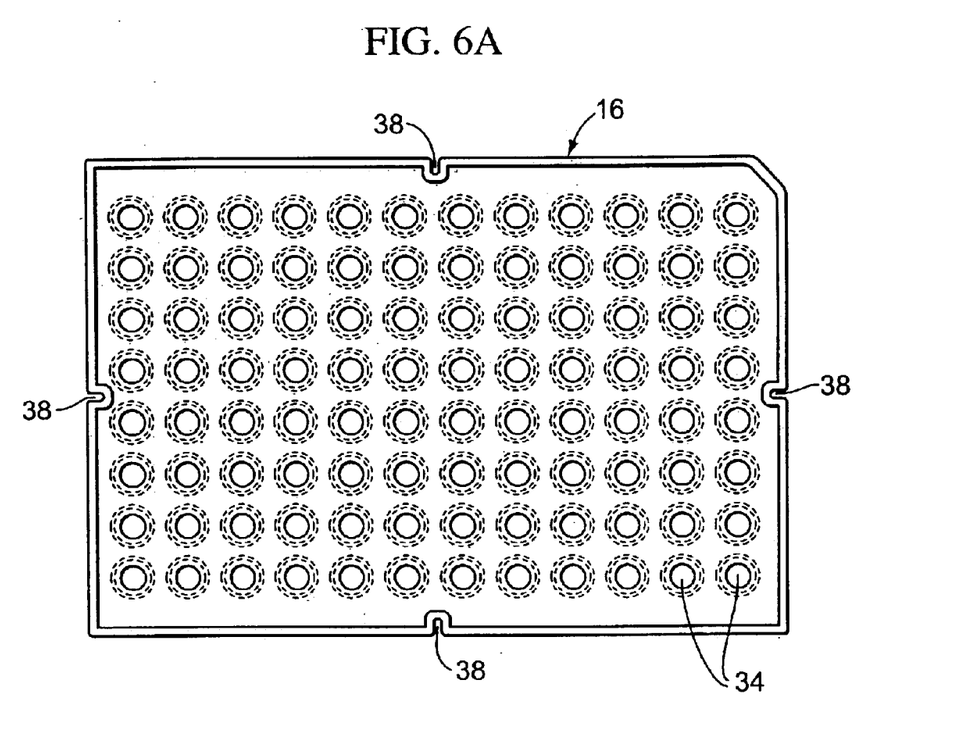

FIGS. 6A and 6B show the platen 16 in top plan and side elevational views, respectively. The platen 16 can include passages or through-holes 34 that are concentric with and directly correspond to the wells of microplate 18. Except for such through-holes, the platen can be configured to substantially cover one or more support. As shown in FIG. 6B, the platen 16 can include ring-shaped projections 36 extending from a major surface 16a, with each ring-shaped projection circumscribing, and further defining, a respective one of the through-holes 34. Such construction can permit access to the individual wells of the microplate through the platen from a region extending above each of the wells of the microplate.

As shown in FIGS. 1A and 1B, an outer circumferential region of each ring-shaped projection 36 of the platen 16 can be configured with a taper along a direction extending away from the major surface 16a of the platen 16 and extending towards supports 12a–h. The taper can facilitate placement and seating of each ring-shaped projection 36 in a corresponding aperture 30 of the die plate 14 upon bringing the platen 16 and die plate 14 together, as shown in FIG. 1B and as described further below. The platen 16 can include slots 38 as shown in FIG. 6A. The slots 38 can have a shape similar to the slots 22 of the supports 12a–h. Slots 38 can assist in properly locating and aligning the platen 16 over the die plate 14 by mating the slots 38 of the platen 16 with the projections 26 of the die plate 14.

The die plate 14, platen 16, and microplate 18 can be formed by any conventional means, for example, by injection molding. According to various embodiments, these components can be constructed of any substantially rigid, water-insoluble, fluid-impervious material that is substantially chemically non-reactive with materials, for example, biochemicals, samples, reagents, and the like, intended for use therewith. The term "substantially rigid" as used herein is intended to mean that the material will resist deformation or warping under a light mechanical or thermal load, although the material may be somewhat elastic. Suitable materials can include, but are not limited to, acrylics, polycarbonates, polypropylenes, and polysulfones.

According to various embodiments, microplate 18 can be an injection molded plastic plate, the length and width of which conform to a commonly used standard, for example, a rectangle of 5.03 inches×3.37 inches (127.8 mm by 85.5 mm). In the illustrated embodiments, wells are formed integrally with the microplate, and can be arranged, for example, in a 12×8 regular rectangular array and spaced 0.9 cm center-to-center. Although the illustrated embodiments show arrangements configured in accordance with the popular 96-well format, the present teachings also contemplate any other number of wells, for example, 12, 24, 48, 192, or 384 wells, laid out in any suitable configuration, for example, square, rectangular, circular, ovoid, or other regular or irregular patterns.

In operation, a die plate 14 can be positioned over a multi-well microplate 18, with each aperture 30 of the die plate 14 located over a corresponding one of the wells of the microplate 18. A plurality of support sheets 12 can be stacked upon the die plate. Alignment of the support sheets 12 with respect to the die plate 14 can be facilitated by way of slots 22 formed in the support sheets 12 and mating projections 26 extending from a surface of the die plate 14 facing the support sheets 12. Each support sheet 12 of the stack can include a plurality of petal-shaped purification members 21, with each petal-shaped purification member 21 of each support sheet 12 being disposed at a position corresponding to a respective one of the wells of the microplate 18. Each of the petal-shaped purification members 21 can be moved between (i) a first position, outside of a corresponding well, and (ii) a second position, extending at least partially into the corresponding well. A platen 16 can be placed over the stack of support sheets 12. The platen 16 can include a major surface 16a facing the support sheets 12, and a plurality of ring-shaped projections 36 can extend outwardly from the major surface 16a toward the support sheets 12. The platen 16 can be moved toward and away from the support sheets 12. Upon moving the platen 16 toward the support sheets 12, the projections 36 can pressingly engage the petal-shaped purification members 21, thereby deflecting the petal-shaped purification members 21 from the first to the second position, as depicted in FIG. 1B. According to various embodiments, the ring-shaped projections 36 of the platen 16 can pressingly engage and deflect the petal-shaped purification members 21 of the support sheets 12 against the holes in the die plate 14 and into the wells of the microplate 18, where the petal-shaped purification members 21 can chemically interact with the contents of the individual wells.

According to various embodiments, one or more chemicals, biochemicals, or purification medium can be present on at least a portion of one or more of the petal-shaped purification members. The petal-shaped purification members can be introduced into respective wells that can contain a first sample, such as a polymerized chain reaction product or DNA sequencing product. The chemicals, biochemicals, and/or purification medium on the petal-shaped purification members can interact with the first sample to bind one or more components of the sample. The chemicals, biochemicals, and/or purification medium on the petal-shaped purification members can bind desirable components, for example, DNA fragments, dsDNA, ssDNA, polynucleotides, oligonucleotides, and the like. Alternately, the chemicals, biochemicals, and/or purification medium on the petal-shaped purification members can bind undesirable reaction products, including fragments, salts, promoters, terminators, reactive dyes, and other undesirable reaction products as known to those of ordinary skill in the art. According to various embodiments, one or more nucleic acids can be purified by and/or immobilized on the petal-shaped purification members. The petal-shaped purification members can be introduced into respective wells that can contain reagents for carrying out polymerase chain reaction (PCR). PCR can then be carried out in the wells. Analysis of the PCR product(s) can then be performed.

According to various embodiments, at least a portion of the petal-shaped purification members can be chemically treated. One or more of the petal-shaped purification members can include one or more biochemicals immobilized thereon. Such biochemicals can include, for example, one or more nucleic acids. In various embodiments, such biochemicals can include one or more DNA-sequencing reagents, such as terminators, primers, or a combination thereof. At least a portion of the petal-shaped purification members can have a purification medium, for example, size-exclusion ion-exchange particles, ion-exchange particles, a size-exclusion resin, or a combination thereof, affixed thereto.

Figure 7:
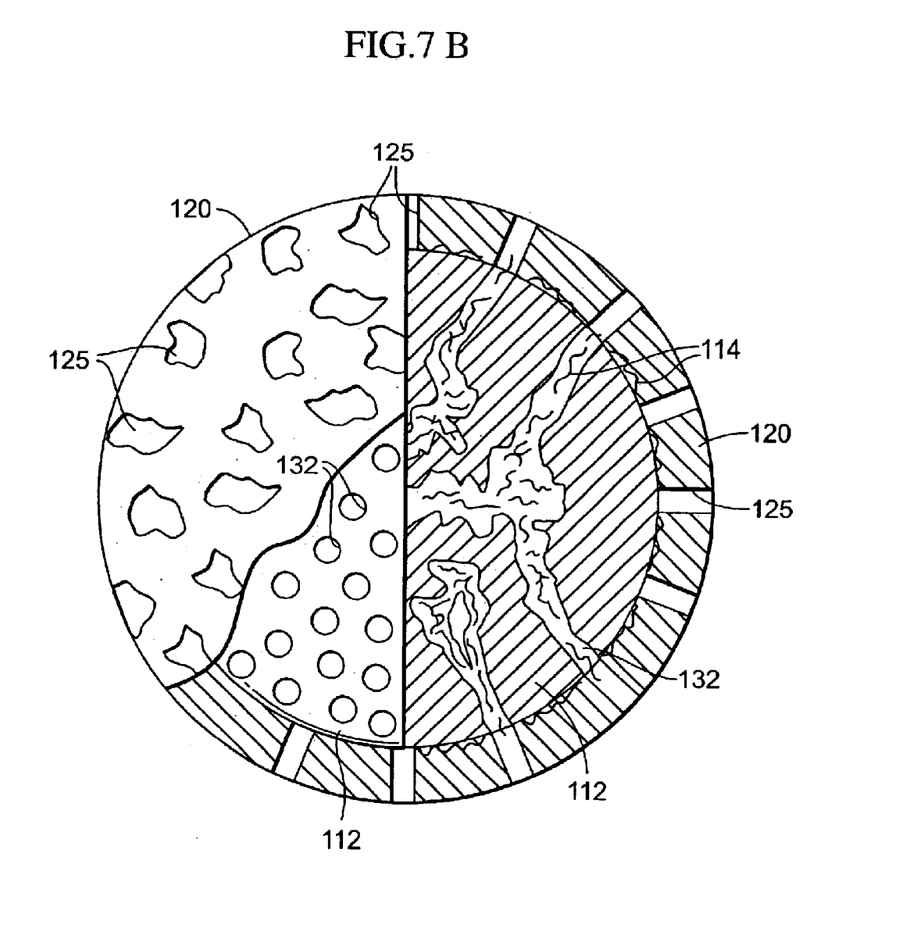
FIG. 7A is a schematic diagram of an interaction of an anion with a size-exclusion ion-exchange particle, according to various embodiments.
FIG. 7B is a cross-sectional view through different lines, of the SEIE particle shown in FIG. 7A and used as a purification material according to various embodiments.
Figure 7A:
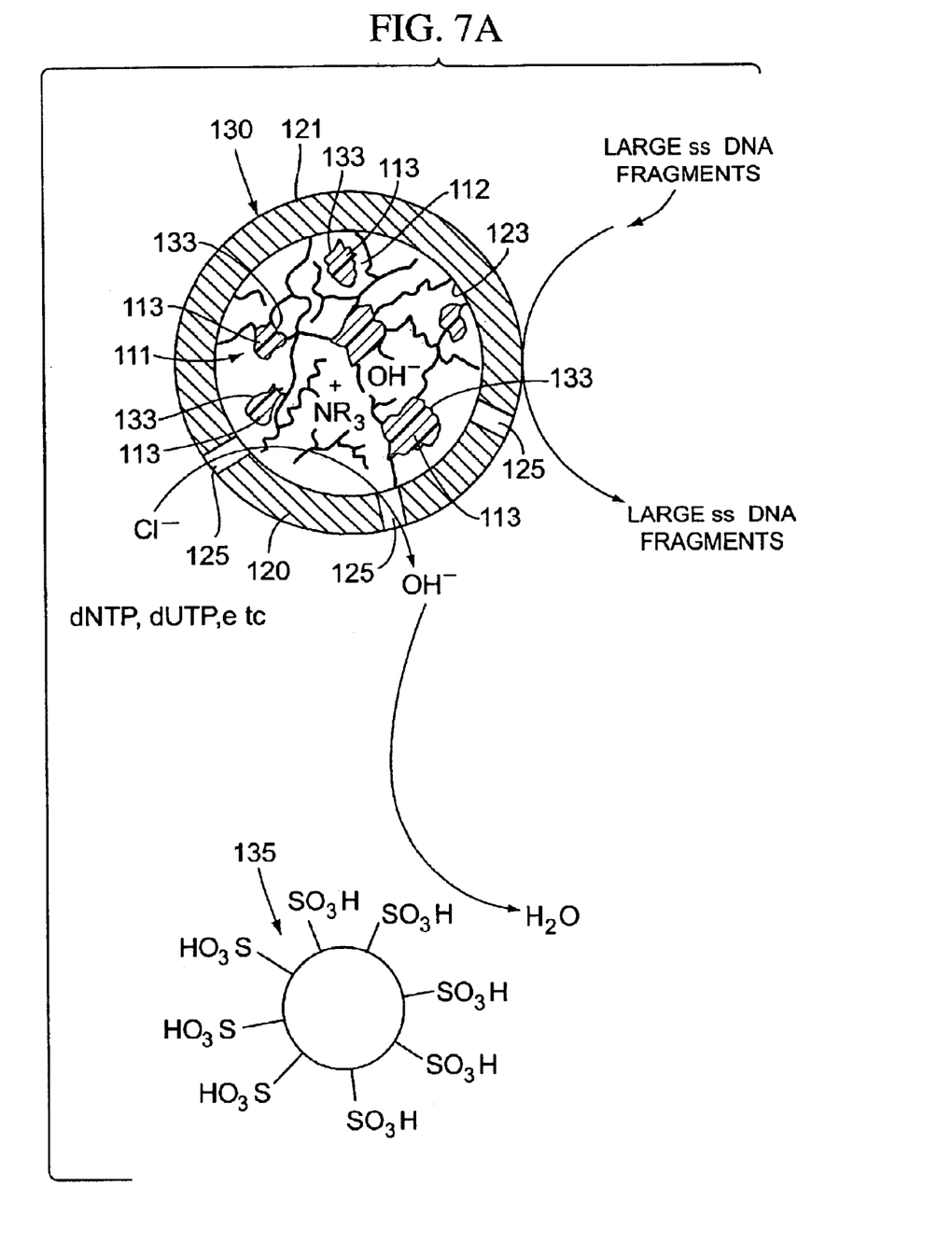

According to various embodiments, the petal-shaped purification members include an ion-exchange material, for example, a size-exclusion ion-exchange (SEIE) particulate material, with or without other chemicals and/or biochemicals. An example of an SEIE particle that can be used as part of a device according to various embodiments, is shown in FIGS. 7A and 7B. An interaction involving the SEIE particle, is shown in FIG. 7A. FIGS. 7A and 7B are not drawn to scale, and the relation between objects in the figures, such as the relation between core pore sizes and shell pore sizes, is not to scale, and can in fact be inverse, such that the core pore size is larger than the shell pore size. As seen in FIGS. 7A and 7B, large molecules, such as long single stranded DNA (ssDNA) fragments, and double stranded DNA (dsDNA), are too large to pass through a pore 125 of a size-exclusion shell 120 of a size-exclusion anion-exchange particle 130. Instead, large molecules can slide past or bounce off an exterior surface 121 of the shell 120, and remain in solution rather than ion-exchanging with the anion-exchange particle 130. Small molecules, such as deoxynucleotide triphosphates (dNTPs), dye-labeled deoxynucleotide triphosphates, dideoxynucelotide triphosphates (ddNTPs), dyelabeled dideoxynucelotide triphosphates, and small ions, such as chlorine, can pass through the pores 125 of the size-exclusion shell 120 and can undergo ion-exchange with anion-exchange resin 113 at or near the interface 123 of the shell and ion-exchange core 111, or within the pores of ion-exchange core 111.

FIG. 7A shows a partial cut-away 133 showing a surface of the ion-exchange core 111 coated with anion-exchange resin 113. The anion-exchange resin 113, for example, a crosslinked, macroporous copolymer of methyl methacrylate and 2-hydroxy-3-methacryloyloxypropyltrimethylammonium chloride, can be present on all internal and external surfaces of the solid core material 112. Together, the anion-exchange resin and solid core material or support 112 form the anion-exchange core 111. Counter-ions released from the anion-exchange core 111, such as hydroxide, can react with a counter-ion, for example, a counter-ion such as a hydroxide ion, of a cation-exchanger 135 that can be provided in a mixture with the SEIE particle 130, to produce a neutral molecule such as water. A more-detailed cutaway view of the shell and core structure is provided in FIG. 7B.

SEIE particles can be used in a mixture, a mixed bed, or a homogeneous bed of particles. Wherein a homogeneous bed of anionic- or cationic-SEIE particles is used, the counter-ion can be released directly into a sample solution upon ion-exchange. In certain cases, the presence of the counter-ion in the sample solution does not affect further processing or reaction of the sample.

According to various embodiments, the selectivity of an SEIE particle can be determined by the nature of the size-exclusion shell, the charge of the ion-exchange core, and the nature of the counter-ion. The properties of the size-exclusion shell can be varied by, for example, choosing appropriate synthesis conditions that can affect the pore size of the resulting shell. Controlling an effective pore size of the size-exclusion shell can allow the SEIE particle to be optimized for different size-exclusion applications.

According to various embodiments, a purification device can include size-exclusion ion-exchange (SEIE) particles embedded in a substrate. The SEIE particles can be ion-exchange particles, as described elsewhere herein, encapsulated by a size-exclusion resin, as described elsewhere herein. An ion-exchange particle can be encapsulated by a size-exclusion resin, for example, by inverse emulsification and polymerization, to form an SEIE particle. For example, an anionic ion-exchange particle can be formed by impregnating polyethyleneimine onto the surface of a solid core material, including all surfaces of the pores of the solid core material. The resultant ion-exchange particle can be encapsulated by a shell of size-exclusion resin, for example, polyacrylamide, to form a size-exclusion anion-exchange (SEAE) particle. By methods known to one of ordinary skill in the art, other anion-exchange resins or cation-exchange resins can be impregnated or retained on at least a portion of the internal surfaces, on at least a portion of the external surface, or on at least a portion of all surfaces of the solid core material of the ion-exchange particle. According to various embodiments, a solid core material capable of ion-exchange can be encapsulated by a size-exclusion resin to form an SEIE particle.

According to various embodiments, the ion-exchange particle can be surface-activated to enhance or aid in formation of the shell around the ion-exchange particle. Surface activation of the ion-exchange particle can include, for example, derivatization of functional groups on the ion-exchange particle by monomers; absorption of polyanions onto the ion-exchange particle by ionic interaction with an ion-exchange resin of the ion-exchange particle; passive adsorption onto the ion-exchange particle of a neutral, water-soluble polymer; or adsorption of a charged initiator on the ion-exchange particle through ionic interaction. Greater details about SEIE particles are described in concurrently filed U.S. patent application Ser. No. 10/414,179 to Lau et al., entitled "Size-Exclusion Ion-Exchange Particles," which is incorporated herein in its entirety by reference.

According to various embodiments, a purification device in the form of a coated stick can be made, wherein the coated stick has SEIE particles embedded in a substrate. The SEIE particles can be encapsulated, attached, adhered, embedded, or otherwise in contact with a substrate, for example, a polymeric substrate, by heat application, by heated extrusion of the substrate in the presence of the particles, by pressure, by physical force, by chemical treatment, by electrical current, by ultrasonication, by molding with the substrate, or by other methods of attachment known to those of ordinary skill in the art, or combinations thereof. For example, as shown and described in concurrently filed U.S. patent application Ser. No. to Hennessey et al, entitled "Device and Method for Purification of Nucleic Acid," which is incorporated herein in its entirety by reference.

According to various embodiments, each support can be a single-layer film or membrane material. Each support can include one or more registration feature, for example, one or more slot formed in each support, to facilitate alignment of the supports with respect to a microplate. The petal-shaped purification members of each support can be resiliently deformable, tending to return to the first position after having been deflected therefrom.

According to various embodiments, a method for biochemical interaction can include immobilizing one or more selected biochemicals on a plurality of petal-shaped purification members, wherein the petal-shaped purification members are disposed in an array on a support. One or more reagents can be introduced into a plurality of wells, wherein the wells are disposed in an array corresponding to the array of petal-shaped purification members. The petal-shaped purification members can be positioned above the plurality of wells so that each petal-shaped purification member is situated above a corresponding one of the plurality of wells. The petal-shaped purification members can be pressingly engaged from a side opposite the wells to simultaneously move the petal-shaped purification members into the corresponding wells, contacting the one or more selected biochemicals on the plurality of petal-shaped purification members with the one or more reagents in the plurality of wells, and permitting a biochemical interaction to take place involving the one or more selected biochemicals and the one or more reagents.

According to various embodiments, a method for biochemical interaction can include providing a plurality of petal-shaped purification members, wherein the petal-shaped purification members are disposed in an array on a support. A microplate including a plurality of wells disposed in an array corresponding to the array of petal-shaped purification members can be provided, wherein one or more selected biochemicals can be placed in the wells of the microplate. The petal-shaped purification members can be positioned above the microplate so that each petal-shaped purification member is situated above a corresponding one of the plurality of wells. The petal-shaped purification members can be pressingly engaged from a side opposite the wells to simultaneously move the petal-shaped purification members into the corresponding wells to contact the one or more selected biochemicals therein. One or more of the selected biochemicals in the wells can be immobilized on the petal-shaped purification members. The petal-shaped purification members with the one or more selected biochemicals immobilized thereon can be withdrawn from the wells.

The method can further include providing a second microplate including a plurality of wells disposed in an array corresponding to the array of petal-shaped purification members, wherein one or more selected reagents is disposed in the wells of the second microplate. The petal-shaped purification members with one or more biochemical immobilized thereon can be positioned above the second microplate so that each petal-shaped purification member is situated above a corresponding one of the plurality of wells. The petal-shaped purification members can be pressingly engaged from a side opposite the second microplate to simultaneously move the petal-shaped purification members into the corresponding wells to contact the one or more reagents therein. A biochemical interaction can take place in the wells involving the one or more selected biochemicals immobilized on the petal-shaped purification members and the one or more selected reagents in the wells. According to various embodiments, the petal-shaped purification members can release the one or more immobilized selected biochemicals from the petal-shaped purification members into the wells.

According to various embodiments, a method for purifying a sample in one or more wells in a plurality of wells disposed in an array is provided. A plurality of petal-shaped purification members disposed in an array on a support can be provided, wherein each of the petal-shaped purification members is at least partially coated with a purification medium, for example, ion-exchange particles, a size-exclusion resin, or size-exclusion ion-exchange particles. The support can be positioned above the microplate such that each petal-shaped purification member is situated above a corresponding one of the plurality of wells. The petal-shaped purification members can be pressingly engaged from a side opposite the wells to simultaneously move the petal-shaped purification members into the corresponding wells to contact the samples in the wells. The petals can remain in contact with the respective samples for a period of time sufficient to remove at least 70%, at least 80%, or at least 90% of the impurities from the sample in the well. After a period of time sufficient to purify the sample, the petal-shaped purification members with the impurities immobilized thereon can be withdrawn from the wells. According to various embodiments, the purification material can adsorb or retain the desired portions of the sample, and leave the impurities in the well.

According to various embodiments, the support sheets containing the petal-shaped purification members with at least a portion of the first sample immobilized thereon can be moved individually or collectively into a position over a second microplate, wherein the petal-shaped purification members can be pressingly engaged by a platen such that the petal-shaped purification members are deflected into the respective wells of the second microplate, wherein the petal-shaped purification members can react with a second sample in the wells of the second microplate to release the immobilized components of the first sample.

According to various embodiments, the petal-shaped purification members can be used for purification of a sample. At least a portion of the petal-shaped purification members can be coated with a purification medium, for example, ion-exchange particles, a size-exclusion resin, or size-exclusion ion-exchange particles, to facilitate purification. As used herein, "resin" includes compositions with the characteristics of a resin or a gel.

According to various embodiments, an ion-exchange particle immobilized on a petal-shaped purification member can be an anionic or cationic material. The ion-exchange particle can be a polymer, cross-linked polymer, or inorganic material, for example, silica. The ion-exchange particle can be a solid core material capable of ion-exchange, or a solid core material treated with an ion-exchange resin. The ion-exchange particle can be surface-activated. The ion-exchange particle can be non-magnetic, paramagnetic, or magnetic. Exemplary ion-exchange particle materials include Macro-Prep® ion-exchange resins from Bio-Rad, and Nucleosil® silica-based ion-exchange resins from Macherey-Nagel.

According to various embodiments wherein the ion-exchange particle includes a solid core material capable of ion-exchange, the solid core material can be macroporous silica, controlled pore glass (CPG), a macroporous polymer microsphere with internal pores, other porous materials as known to one of ordinary skill in the art, or a combination thereof. The solid core material can have various surface features, including, for example, pores, crevices, cracks, or depressions. The solid core material can include sodium oxide, silicon dioxide, sodium borate, or a combination thereof. The solid core material can be modified to be capable of ion-exchange, for example, cation-exchange or anion-exchange. Modification of the solid core material can include treatment of the solid core material to form cationic or anionic substituent groups on the surfaces of the solid core material. As used herein, the term "surface" can include an external surface and internal surfaces, for example, the surfaces of voids or pores within the solid core material. The solid core material can be modified to include quaternarized functional groups, at least one carboxylic acid group, at least one sulfonic acid group, other cationic or anionic functional groups known to one of ordinary skill in the art, or a combination thereof on the surface of the solid core material. According to various embodiments, the solid core material can be porous, microporous, or macroporous. The solid core material can have an average pore size of less than or equal to 1000 Angstroms, from 100 Angstroms to 1000 Angstroms, or less than or equal to 100 Angstroms. The average diameter of the solid core material can be from 0.1 m to 100 $\mu$m, from 1 $\mu$m to 50 $\mu$m, or from 2 $\mu$m to 20 $\mu$m, according to various embodiments. The average diameter of the solid core material can be 100 $\mu$m or less, 50 $\mu$m or less, or 20 $\mu$m or less.

According to various embodiments, a solid core material can adsorb an ion-exchange resin onto the external surface, internal surface, or both the external and the internal surface of the solid core material to form an ion-exchange particle. The ion-exchange resin can be a cation-exchange resin or an anion-exchange resin. The ion-exchange resin can include quaternarized functional groups, at least one carboxylic acid group, at least one sulfonic acid group, or a combination thereof. Suitable anion-exchange resins and cation-exchange resins are known to one of ordinary skill in the art.

According to various embodiments, the ion-exchange resin can be sequestered into the pores of the solid core material, for example, a macroporous silica particle. Filling at least a portion of the pores of the solid core material and/or coating the external surface of the solid core material with the ion-exchange resin can increase the ion-exchange capacity of the ion-exchange particle over traditional ion-exchange resins. The ion-exchange capacity of the ion-exchange particle can be improved by increasing a mass of ion-exchange resin, such as quaternary ammonium resin, on the external surface and/or on the internal surfaces of the pores of the solid core material of the ion-exchange particle. The ion-exchange capacity of the ion-exchange particle can be improved by selection of cationic or anionic functional groups on the external surface, internal surfaces of the pores, or both internal surfaces and external surface of the solid core material.

According to various embodiments, the ion-exchange resin can be formed in situ on the solid core material. The ion-exchange resin can be the product of one or more monomer, one or more polymer, or a combination thereof, according to various embodiments. For example, a solid core material of $SiO_2$ having an average pore size of 1000 Angstroms, a void volume of 0.95 cc/g, and a diameter of 5 $\mu$m, can be added to a solution of polyethyleneimine in methanol and incubated for a time sufficient to impregnate the polyethyleneimine on all internal and external surfaces of the solid core material. According to various embodiments, polyethyleneimine can be adsorbed due to hydrogen bonding with silanol groups in the solid core material. The adsorbed polyethyleneimine can be reacted with a second monomer, such as, for example, 1,3-dibromopropane, in a solvent, for example, dioxane, followed by placement in water, to form a quaternary ammonium gel that functions as an anion-exchange resin on the solid core material, forming an ion-exchange particle. Other methods can be used and are described, for example, in concurrently filed U.S. application Ser. No. 10/414,179, to Lau et al., entitled "SIZE-EXCLUSION ION-EXCHANGE PARTICLES," which is incorporated herein in its entirety by reference. Such methods include methods used to impregnate or retain other anion-exchange resins or cation-exchange resins on at least a portion of the internal surfaces, on at least a portion of the external surface, or on at least a portion of all surfaces of the solid core material of the ion-exchange particle.

According to various embodiments, purification of a sample with an ion-exchange particle can be achieved by ion-exchange. Displacement of counter-ions from the ion-exchange particle during ion-exchange can release a large number of counter-ions into a sample solution. According to various embodiments, anionic ion-exchange particles and cationic ion-exchange particles can both be present during purification of a sample such that counterions of the ion-exchange particles react to form a neutral molecule, for example, water. The ion-exchange particles can both be present on a petal-shaped purification member, or at least one of cationic or anionic ion-exchange particles can be present, for example, in the sample.

According to various embodiments, an ion-exchange particle can contain a lower mobility counter-ion, for example, octane sulfonate. An ion-exchange particle can contain a volatile counter-ion, for example, acetate, which can later be removed from a sample solution. According to various embodiments, the counter-ion for an anionic ion-exchange particle can be, for example, a halide or hydroxide. According to various embodiments, the counter-ion for a cationic ion-exchange particle can be, for example, hydrogen.

One or more ion-exchange particle can be affixed or attached to a petal-shaped purification member by adhering, pressing, or otherwise attaching a particle to the member. For example, the ion-exchange particle and/or the petal-shaped purification member can be heated or chemically treated, and the ion-exchange particle pressed into the petal-shaped purification member, affixing the particle to the petal-shaped purification member. According to various embodiments, the ion-exchange particles can be placed in a monomer solution including at least one polymerizable polymer and one or more of a catalyst, initiator, cross-linker, chain stopper, surfactant, terminator, promoter, buffer, accelerator, or a combination thereof. The monomer solution can be capable of polymerizing or cross-linking at about room temperature. The monomer solution can be capable of polymerizing upon application of heat, application of radiation, addition of a catalyst, addition of an initiator, or a combination thereof. A petal-shaped purification member can be inserted into the monomer solution including the ion-exchange particles, and the monomer solution can be polymerized and/or cross-linked to adhere the ion-exchange particles to the petal-shaped purification member. Other methods of attaching the ion-exchange particles to the petal-shaped purification members will be apparent to those of ordinary skill in the art.

According to various embodiments, the monomer solution can be capable of forming a size-exclusion resin. A size-exclusion resin with or without ion-exchange particles therein can be coated on at least a portion of one or more of the petal-shaped purification members. The size-exclusion resin can be a cross-linked or polymerized, monomer such as a hydrogel. As used herein, unless otherwise specified, the terms "polymer," "polymerization," "polymerize," "cross-linked product," "cross-linking," "cross-link" and other like terms are meant to include both polymerization products and methods, and cross-linked products and methods wherein the resultant product is a three-dimensional structure, as opposed to, for example, a linear polymer. The degree of cross-linking of the size-exclusion resin can be varied in order to vary the size of the pores of the size-exclusion resin. For example, the pore size of the size-exclusion resin can be large enough to allow relatively small ions, such as, for example, chloride, nucleotides, or other small molecules, to permeate through the size-exclusion resin. The pore size of the size-exclusion resin can be small enough to prevent any relatively large molecules, such as 100 nt DNA fragment or larger, from permeating through the size-exclusion resin. According to various embodiments, the size-exclusion resin can be hydrophilic to reduce passive adsorption or absorption of biomolecules such as, for example, ssDNA fragments.

According to various embodiments, a size-exclusion resin can be a cross-linked product of two or more reactive monomeric units. The monomeric units can be water-soluble monomeric units. As used herein, the term "water-soluble" includes materials with any degree of water solubility from slightly water-soluble to highly water-soluble, and materials that are swellable in water. The monomeric units can be nitrogen-containing, oxygen-containing, or both. The size-exclusion resin can be a homopolymer or a copolymer. The size-exclusion resin can be the reaction product of an acrylamide, such as polyacrylamide, polymethylmethacrylate, polyethylmethacrylate, or polymethacrylate. The size-exclusion resin can be a reaction product of acrylamide and N,N'-methylenebisacrylamide. According to various embodiments, exemplary water-soluble polymers can include, but are not limited to, polyacrylamide, poly(N-methylacrylamide), poly(N,N-dimethylacrylamide), poly(N-vinylformamide), poly(N-vinylacetamide), poly(N-methyl-N-vinylacetamide), poly (vinylalcohol), poly(hydroxyethyl (meth)acrylate), poly (vinypyrrolidone), methylcellulose, ethylcellulose, other suitable polymers capable of cross-linking as known to one of ordinary skill in the art, or a combination thereof. The size-exclusion resin can be neutral, anionic, or cationic. According to various embodiments, the size-exclusion resin can be hydrophilic. The size-exclusion resin can be a cross-linked polymer network of polymers capable of swelling in water, for example, hydrogels. Exemplary hydrogels are described, for example, in U.S. Pat. No. 6,380,456 B1, incorporated herein in its entirety by reference. The size-exclusion resin, once formed, can be non-water soluble. According to various embodiments, the size-exclusion resin can prevent adsorption of ssDNA fragments and/or double-stranded DNA (dsDNA) fragments.

According to various embodiments, the size-exclusion resin can be formed with pores of a pre-determined size. The pores can be of the same or varying size. The pores can function as the size-exclusion factor for preventing molecules larger than a certain size from passing through the size-exclusion resin to the ion-exchange core which is encapsulated by the size-exclusion resin. According to various embodiments, the size-exclusion resin can be formed by cross-linking one or more reactive monomer by addition of a cross-linker, for example, N,N'-methylenebisacrylamide, a free-radical initiator, a chain-stopper, a surfactant, a catalyst, a terminator, a promoter, a buffer, an accelerator, or a combination thereof. A cross-linker or initiator can be added in an amount of from 1.0 mol % to 95 mol %. According to various embodiments, the cross-linker or initiator can be added in an amount of from 1.0 mol % to 50 mol %, from 2.0 mol % to 20 mol %, from 5 mol % to 15 mol %, or from 10 mol % to 12 mol %. The amount of cross-linker or initiator used to form the size-exclusion resin is at least one factor in determining the size of the pores of the size-exclusion resin, and the size-exclusion ability of the size-exclusion resin. According to various embodiments, the choice of cross-linker or initiator, and/or selection of the reaction conditions, can control the amount of cross-linking of the size-exclusion resin. For example, various multifunctional cross-linkers can be used that have varying amounts of functionality. The appropriate amount of a cross-linker to use to form a desired size-exclusion resin pore size can be determined by those of ordinary skill in the art based on the functionality of the cross-linker chosen, the reaction conditions, and other factors as known to those of ordinary skill in the art. The monomer solution can be capable of polymerizing or cross-linking at about room temperature. The monomer solution can be capable of polymerizing upon application of heat, application of radiation, addition of a catalyst, addition of an initiator, or a combination thereof. The resultant size-exclusion resin can have a pore size equal to or smaller than a 10 nt ssDNA, or equal to or smaller than a 100 nt ssDNA. Other suitable pore sizes can be achieved by the above methods or other methods as known to those of ordinary skill in the art.

According to various embodiments, a size-exclusion resin can form a coating, for example, a shell, on an ion-exchange particle, forming a size-exclusion ion-exchange (SEIE) particle. The size-exclusion resin can restrict the ability of molecules to interact with the ion-exchange particle, combining the high selectivity and binding ability of ion-exchange chromatography (IEC) with the size-exclusion of size-exclusion chromatography (SEC).

According to various embodiments, size-exclusion ion-exchange (SEIE) particles can be coated on or attached to a petal-shaped purification member. An ion-exchange particle as described herein can be encapsulated by a size-exclusion resin as described herein, for example, by inverse emulsification and polymerization, to form an SEIE particle. For example, an anionic ion-exchange particle can be formed by impregnating polyethyleneimine onto the surface of a solid core material, including all surfaces of the pores of the solid core material. The resultant ion-exchange particle can be encapsulated by a shell of size-exclusion resin, for example, polyacrylamide, to form a size-exclusion anion-exchange (SEAE) particle. By methods known to one of ordinary skill in the art, other anion-exchange resins or cation-exchange resins can be impregnated or retained on at least a portion of the internal surfaces, on at least a portion of the external surface, or on at least a portion of all surfaces of the solid core material of the ion-exchange particle. According to various embodiments, a solid core material capable of ion-exchange can be encapsulated by a size-exclusion resin to form an SEIE particle. More details on the formation, use and composition of SEIE particles are set forth in concurrently filed U.S. application Ser. No. 10/414,179, to Lau et al., entitled "SIZE-EXCLUSION ION-EXCHANGE PARTICLES," and in concurrently filed U.S. application Ser. No. 10/413,797, to Hennessey et al. entitled "DEVICE AND METHOD FOR PURIFICATION OF NUCLEIC ACIDS," both of which are incorporated herein in their entireties by reference.

According to various embodiments, the ion-exchange particle can be surface-activated to enhance or aid in formation of the shell around the ion-exchange particle. Surface activation of the ion-exchange particle can include, for example, derivatization of functional groups on the ion-exchange particle by monomers; absorption of polyanions onto the ion-exchange particle by ionic interaction with an ion-exchange resin of the ion-exchange particle; passive adsorption onto the ion-exchange particle of a neutral, water-soluble polymer; or adsorption of a charged initiator on the ion-exchange particle through ionic interaction. Methods of surface activation of an ion-exchange particle are set forth in detail in related U.S. application Ser. No. 10/414,179, to Lau et al. entitled "SIZE-EXCLUSION ION-EXCHANGE PARTICLES," which is incorporated herein by reference in its entirety.

According to various embodiments, a size-exclusion resin shell can be formed on an ion-exchange particle wherein the shell has a thickness of from 2% to 300% of the diameter of the ion-exchange particle. The shell can have a thickness of from 25% to 200% of the diameter of the ion-exchange particle. The thickness of the shell can vary over the surface of the ion-exchange particle, or the thickness of the shell can be uniform over the surface of the ion-exchange particle. The shell can at least partially encapsulate the ion-exchange particle. The shell material can at least partially fill one or more pore or surface feature, for example cracks, of the ion-exchange particle. For example, all internal and external surfaces of the ion-exchange particle can be coated with a monomer suitable for forming a shell. The monomer can be reacted with one or more of a second monomer, a catalyst, or an initiator to form a cross-linked size-exclusion polymer on all surfaces of the ion-exchange particle, with the outermost surface of the size-exclusion polymer forming a shell. Large molecules can not contact the ion-exchange particle because of the presence of the polymer forming the size-exclusion shell on all surfaces of the ion-exchange particle.

Large molecules, such as single strand DNA (ssDNA) fragments, can be too large to pass through a pore of the size-exclusion shell surrounding the ion-exchange particle. Such large molecules can slide past or bounce off exterior surface of the shell, and can remain in solution. Small molecules, for example, deoxynucleotide triphosphates, and small ions, for example, chlorine, can pass through the size-exclusion shell and undergo ion-exchange with the ion-exchange particle at the interface of the shell and ion-exchange particle. The small molecules can undergo ion-exchange with the ion-exchange particle on all internal and external surfaces of the particle. The ion-exchange particle can be a solid core material coated with an ion-exchange resin. According to various embodiments, counter-ions released from the ion-exchange particle can react with the counter-ion of an ion-exchanger to produce a neutral molecule, such as water. The ion-exchanger can be present on the petal-shaped purification member, or in the sample solution. The ion-exchanger can be another SEIE particle.

According to various embodiments wherein about 50% or more of the pores of the size-exclusion resin or shell of a SEIE particle have a pore size capable of excluding a molecule equal to or larger than a 100 nt ssDNA, nucleotides, oligonucleotide primers less than 100 nt in size, and buffer salts can pass through the size-exclusion resin while 100 nt or larger molecules are deflected by the size-exclusion resin. Wherein 50% or more of the pores have a pore size capable of excluding a molecule equal to or larger than a 100 nt ssDNA, the size-exclusion resin can be used for purification of biological samples, for example, PCR products, to separate larger DNA, for example dsDNA, from ssDNA, free nucleotides, and salts.

According to various embodiments wherein 50% or more of the pores of the size-exclusion resin or shell of a SEIE particle have a pore size capable of excluding a molecule equal to or larger than 10 nt ssDNA, salts and nucleotides, for example, present in a sample to be purified, can pass through the size-exclusion resin. Wherein 50% or more of the pores of the size-exclusion resin have a pore size capable of excluding a molecule equal to or larger than 10 nt, the size-exclusion resin can be used for purification of biological samples, for example, from a sequencing reaction. Purification of a sequencing reaction sample can remove dye-labeled dideoxynucleotides and salts from the sequencing reaction sample, leaving a purified sample containing ssDNA in an amount of 70% or more, 80% or more, 90% or more, or 95% or more of the eluted sample volume.

According to various embodiments, a sample for purification can be a PCR product solution containing, for example, buffer salts, metal ions, polymerase, nucleotides, oligonucleotide primers, and other components. According to various embodiments, PCR products can be used in subsequent enzymatic reactions that can be sensitive to at least some of the artifacts found in a sample solution containing the PCR products. For example, free nucleotides and oligonucleotide primers can interfere with downstream enzymatic reactions. According to various embodiments, a size-exclusion resin or SEIE particle in a purification device can have a pore size capable of excluding a molecule equal to or larger than a 100 nt ssDNA, allowing nucleotides, oligonucleotide primers less than about 100 nt in size, and buffer salts to pass through the size-exclusion resin. 100 nt or larger molecules can remain in the sample solution.

According to various embodiments, at least 50% or more of the surface of the size-exclusion resin or SEIE particle shell is capable of excluding a molecule equal to or larger than a 100 nt ssDNA, and allowing nucleotides, oligonucleotide primers, and buffer salts less than 100 nt in size to pass through the size-exclusion resin, or though the shell of the SEIE particle to the ion-exchange core. The resulting purified sample solution can contain purified PCR products in a desalted environment, and can be used in downstream reactions and analyses. According to various embodiments, PCR purification can be directed toward purifying larger dsDNA separate from smaller ssDNA, free nucleotides, and salts. PCR product purification using a petal-shaped purification member having one or more of ion-exchange particles, a size-exclusion resin, or SEIE particles affixed thereto can isolate a 250–600 bp amplicon, can remove 44 nt primers and/or nucleotides, or both isolate and remove.

According to various embodiments, a sample for purification can be a DNA sequencing reaction solution containing, for example, buffer salts, metal ions, enzymes, polymerase, nucleotides, oligonucleotide primers, and other components. Purification of sequencing reaction solutions can have different requirements than purification of PCR reaction solutions. For example, according to various embodiments, finished sequencing reactions can contain residual dye-labeled dideoxynucleotides (terminators) that can be removed prior to electrophoretic analysis and DNA sequencing or basecalling. Failure to remove terminators can result in "blobs" that can cause errors in DNA sequencing or basecalling. According to various embodiments, capillary sequencers can use electrokinetic injection as a means to introduce DNA sequencing reaction samples. The presence of salts in the samples can effect the introduction of the sample into the capillary. DNA sequencing reaction samples can be highly desalted by purification with ion-exchange particles, a size-exclusion resin, or SEIE particles. According to various embodiments, a sample solution purified as described herein can have a salt connection less than or equal to about 100 $\mu$M, or less than or equal to 50 $\mu$M. A purified sample solution can be suitable for electrokinetic capillary injection. The size-exclusion resin or shell of the SEIE particle can be capable of excluding a molecule equal to or larger than a 10 nt ssDNA, allowing smaller molecules, for example, salts and nucleotides, in a sample solution to pass through the size-exclusion resin or shell. According to various embodiments, about 50% or more of the surface of the size-exclusion resin or SEIE shell can be capable of excluding a molecule equal to or larger than about a 10 nt ssDNA, allowing smaller molecules, for example, salts and dye-labeled nucleotides, to be removed from the sample solution, and leaving ssDNA free in the sample solution. A sequencing reaction purification can separate ssDNA, for example, ssDNA of from about 10 nt to about 800 nt in size, from, for example, dye-labeled nucleotides and salts.

According to various embodiments, a binding site array assembly can be constructed to utilize a plurality of support sheets between a die and a platen to maximize sample exposure to support sheets. The binding site assembly can be used to "fish" out matching sequences from the contents of the microplate wells onto one or more support sheets. Each "exposed" support sheet can then be removed from the binding site array assembly and reassembled between a second die and platen for elution of the labeled samples into another (clean) microplate.

According to various embodiments, the upper portions of the microplate wells can be configured to act in place of the die plate, thus eliminating the die plate from the above-described assembly. Many varieties of microplates, available from different suppliers, can be accommodated by the incorporation of a spring-loaded centering means within the basic assembly.

It will be appreciated by those skilled in the art that the present teachings provide a method of delivering to or removing from a sample well salts, dyes, DNA, terminators, primers, or other components useful for, or resulting from, PCR or DNA sequencing; a facility for the exposure of one or more discreet supports to an array of individual samples; and, a tool for moving and/or transferring large numbers of labeled samples at a time. The present teachings further provides the ability to capture nucleotides or other biological samples on multiple binding sites on a support within a standard laboratory microplate format, and enables subsequent release of the nucleotides or other biological samples from the support, also within the microplate format. The present teachings further provides a method of purifying a PCR product or DNA sequencing reaction product in bulk.

The present teachings provide a plurality of discreet, labeled, petal-shaped purification members and their support in a single deformable film or membrane. This design can eliminate many handling and alignment issues associated with stacking and placing many post/array assemblies with densely packed probes, for example, twelve, into the distinct wells, for example, 96, of a standard microtiter plate.

All publications and patent applications referred to herein are hereby incorporated by in their entirety, and to the same extent as if each individual publication or patent on was specifically and individually indicated to be incorporated by reference.

It will be apparent to those skilled in the art that various modifications and variations de to various embodiments described herein without departing from the spirit or scope resent teachings. Thus, it is intended that various embodiments cover other ions and variations of various embodiments within the scope of the present teachings.

It is claimed:

1. An analyte-manipulation apparatus, comprising:
   a plurality of wells defining an array;
   a support comprising a plurality of petal-shaped purification members formed therein at positions corresponding to said wells of said array, wherein said petal-shaped purification members comprise an ion-exchange material and a size-exclusion resin;
   wherein each of said petal-shaped purification members is movable between a first position outside said wells, and a second position inside said wells;
   a platen comprising a plurality of ring-shaped projections to pressingly engage said petal-shaped purification members from said first to said second position.

2. The apparatus of claim 1, wherein said platen and each of said ring-shaped projections defines a passage extending longitudinally through each ring-shaped projection and through said platen.

3. The apparatus of claim 1, wherein said ion-exchange material is ion-exchange particles affixed to said petal-shaped purification members.

4. The apparatus of claim 3, wherein said ion-exchange material and said petal-shaped purification members are at least partially coated with a size-exclusion resin.

5. The apparatus of claim 1, wherein at least a portion of one or more of said petal-shaped purification members includes size-exclusion ion-exchange particles affixed thereto.

6. The apparatus of claim 1, wherein said petal-shaped purification members are resiliently deformable, tending to return to said first position after having been deflected therefrom.

7. The apparatus of claim 1, wherein the support includes one or more registration features facilitating alignment of the support with respect to the microplate.

8. The apparatus of claim 7, wherein said one or more registration features comprises one or more slots formed in the support.

9. The apparatus of claim 1, wherein each of said ring-shaped projections tapers in a direction away from said major surface.

10. An analyte-manipulation apparatus, comprising:
a plurality of wells defining an array, each of said wells including an opening at an upper end thereof;
a stack of supports disposed above said openings, each support of said stack including a plurality of petal-shaped purification members formed therein, and each petal-shaped purification member of each support being disposed at a position corresponding to a respective one of said wells of said array, said petal-shaped purification members including an ion-exchange material;
wherein each of said petal-shaped purification members is movable between (i) a first position, outside of a corresponding respective well, and (ii) a second position, extending at least partially into such corresponding respective well;
a platen including a major surface facing said stack of supports and a plurality of ring-shaped projections extending outwardly from said major surface, said platen being adapted for movement toward and away from said stack of supports, whereby upon moving said platen toward said stack of supports, said projections can pressingly engage said petal-shaped purification members, thereby deflecting said petal-shaped purification members from said first to said second position.

11. The apparatus of claim 10, wherein said stack includes at least three of said supports.

12. The apparatus of claim 10, wherein at least a portion of one or more of said petal-shaped purification members includes ion-exchange particles affixed thereto.

13. The apparatus of claim 10, wherein at least a portion of one or more of said petal-shaped purification members is coated with a size-exclusion resin.

14. The apparatus of claim 10, wherein at least a portion of one or more of said petal-shaped purification members includes size-exclusion ion-exchange particles affixed thereto.

15. A method for biochemical interactions, comprising:
providing a plurality of petal-shaped purification members, wherein the petal-shaped purification members are disposed in an array on a support and include an ion-exchange material;
providing a microplate including a plurality of wells disposed in an array corresponding to the array of petal-shaped purification members;
placing respective samples in the wells of the microplate;
positioning the petal-shaped purification members above the microplate, so that each petal-shaped purification member is situated above a corresponding one of the plurality of wells;
pressingly engaging the petal-shaped purification members from a side opposite that of the wells, so that the petal-shaped purification members are simultaneously moved into their corresponding wells, thereby contacting the respective samples therein;
purifying the respective samples by contacting the respective samples with the ion-exchange material of the petal-shaped purification members, in the wells; and
withdrawing the petal-shaped purification members from the wells.

16. A method of claim 15, wherein at least a portion of one or more of the petal-shaped purification members includes ion-exchange particles embedded therein.

17. The method of claim 15, wherein at least a portion of one or more of said petal-shaped purification members is coated with a size-exclusion resin.

18. The method of claim 15, wherein at least a portion of one or more of said petal-shaped purification members includes size-exclusion ion-exchange particles affixed thereto.

19. A method for purification of a sample, comprising:
providing a plurality of petal-shaped purification members, wherein the petal-shaped purification members are disposed in an array on the support;
providing a microplate including a plurality of wells disposed in an array corresponding to the array of petal-shaped purification members;
placing respective samples for purification in the wells of the microplate, the respective samples including one or more components;
positioning the petal-shaped purification members above the microplate, so that each petal-shaped purification member is situated above a corresponding one of the plurality of wells;
pressing engaging the petal-shaped purification members from a side opposite that of the wells, so that the petal-shaped purification members are simultaneously moved into their corresponding wells, thereby contacting the respective samples for purification therein;
ion-exchanging one or more components of the sample with the ion-exchange material of the petal-shaped purification members, in the wells; and
withdrawing the petal-shaped purification members from the wells.

20. The method of claim 19, wherein the ion-exchange material includes size-exclusion ion-exchange particles.

21. The method of claim 19, wherein the ion-exchange material includes size-exclusion ion-exchange particles embedded in a polymeric substrate.

22. The method of claim 19, wherein at least a portion of one or more of said petal-shaped purification members includes size-exclusion resin and ion-exchange particles.

23. The method of claim 19, further comprising immobilizing at least one of the one or more components on one or more of said petal-shaped purification members.

* * * * *